United States Patent [19]

Beers

[11] Patent Number: 5,467,187
[45] Date of Patent: Nov. 14, 1995

[54] AUTOMATIC CALIBRATION SYSTEM FOR TURBIDIMETERS USING A PULSING FLUID FLOW TO RECIPROCATE A STANDARD IN A CUVETTE

[75] Inventor: Howard L. Beers, North Fort Myers, Fla.

[73] Assignee: HF Scientific, Inc., Fort Myers, Fla.

[21] Appl. No.: 315,112

[22] Filed: Sep. 29, 1994

[51] Int. Cl.$^6$ .................................................... G01J 1/02
[52] U.S. Cl. ..................... 356/243; 356/339; 356/434; 356/442
[58] Field of Search .................. 256/243, 337–342, 256/432, 434, 436, 442

[56] References Cited

U.S. PATENT DOCUMENTS

| | | | |
|---|---|---|---|
| 4,158,505 | 6/1979 | Mathisen et al. | 356/308 |
| 4,566,798 | 1/1986 | Haas | 356/243 |
| 4,799,799 | 1/1989 | Sapko et al. | 356/446 |
| 4,878,755 | 11/1989 | Siegmund et al. | 356/382 |
| 5,120,979 | 6/1992 | Mersch | 356/339 |

Primary Examiner—Richard A. Rosenberger
Assistant Examiner—Jason D. Eisenberg
Attorney, Agent, or Firm—William E. Noonan

[57] ABSTRACT

An automatic calibration system is disclosed for an apparatus that measures the presence of s selected component in a test liquid sample. The system includes a transparent test liquid holder having an inlet and outlet for conducting a test liquid into and out of the holder. There is a transparent calibration element immersed in a test liquid in the holder and including a first sealed compartment that contains a full scale calibration standard and a second sealed compartment that contains a zero calibration standard. A pulsed flow of the test liquid is directed through the holder from the inlet to the outlet to reciprocate the calibration element within the holder. A light source is directed at the holder for establishing an incident beam of light that sequentially strikes the full scale standard, the zero standard, and a test liquid sample as the calibration element reciprocates through the holder. The light, emitted from the full scale and zero standards and the liquid sample is sensed and respective signals representative of the intensity of the emitted light are generated. The signals are processed to determine a calibrated measure of the selected component in the test liquid sample.

16 Claims, 4 Drawing Sheets

AUTOMATIC CALIBRATION SYSTEM FOR TURBIDIMETERS USING A PULSING FLUID FLOW TO RECIPROCATE A STANDARD IN A CUVETTE

FIELD OF THE INVENTION

This invention relates to an automatic calibration system for an apparatus that measures the presence of a selected component in a test fluid sample. The system is particularly effective for use in turbidimeters, photometers and similar devices.

BACKGROUND OF THE INVENTION

Turbidimeters are widely used to test the effectiveness of water filtration systems. Governmental regulations require that such instruments provide highly accurate readings. Unfortunately, a considerable degree of effort and expense is typically required to maintain this accuracy. Present turbidimeters must employ an incandescent light source, which utilizes a spectrum of light broad enough to measure small particles. Incandescent light sources cannot be modulated and must remain on constantly. This often causes relatively rapid deterioration of the light source and inaccurate measurements. To compensate for this, as well as for other factors such as sensor deterioration, electronic drift, variations resulting from standard container glassware, and the accumulation of dirt and other impurities on the test sample cuvette, the turbidimeter must be cleaned and re-calibrated on a regular basis. This usually necessitates costly and inconvenient manual intervention, as well as equipment down-time.

Instruments have been developed that perform re-calibration internally through means of appropriate software. See my co-pending patent application Ser. No. 008,874, filed Jan. 22, 1993. However, such re-calibration still involves a considerable degree of human intervention with attendant inconvenience, delay and expense. The operator must manually remove the cuvette and add an appropriate calibration standard. This is a messy procedure that involves the handling and mixing of carcinogenic substances such as Formazin. Additionally, this procedure has the disadvantage of viewing the standard solution through different glassware which introduces further inaccuracies into the system. And periodically, the surface of the cuvette must be cleaned and worn lamps or sensors replaced. In my above-referenced application, I have provided for a readily replaceable light source for a turbidimeter. However, even this light source deteriorates over time and eventually may cause inaccurate measurements. To date, a convenient system is not known for automatically and continuously re-calibrating turbidimeters and similar instruments between periodic maintenance checks so that a consistent accuracy is maintained.

SUMMARY OF THE INVENTION

It is therefore an object of the present invention to provide a system for automatically and accurately calibrating turbidimeters and other instruments that measure the presence of a selected component in a test fluid sample.

It is a further object of this invention to provide a calibration system that continuously re-calibrates a turbidimeter or similar instrument so that accurate measurements of a selected component in a sample fluid stream are consistently maintained.

It is a further object of this invention to provide a calibration system that automatically compensates for light source aging, sensor deterioration, deviations resulting from different glassware used by the calibration standards and test sample, and other optical or electronic difficulties.

It is a further object of this invention to provide a calibration system that automatically cleans the interior surface of a test fluid holder to provide for improved accurate measurement of light transmitted through the holder.

It is a further object of this invention to provide an automatic calibration system that significantly reduces the delays, expense, human intervention and inconvenience previously associated with maintaining and re-calibrating turbidimeters and similar instruments.

It is a further object of this invention to provide an automatic calibration system that may be quickly and conveniently incorporated into a wide variety of test instruments and that is convenient to repair or replace when necessary.

This invention results from a realization that in nephelometric instruments, factors unrelated to turbidity, such as electronic deterioration, the use of different glassware to hold the test sample and calibration standards, and optical contamination, equally affect the output signals generated by the test sample and the calibration standards. This principle likewise applies to other instruments which use light to measure the presence of a selected component in a test sample. Accordingly, I have determined that a calibrated measure of the presence of a selected component in a test sample may be derived using the following formula:

$$\frac{\text{test sample intensity} - \text{zero standard intensity}}{\text{full scale intensity} - \text{zero standard intensity}} \times$$

(full scale calibration standard)

This invention further results from the realization that the test instrument may be continuously and accurately recalibrated by taking light intensity measurements and performing the above calculation during each of a succession of pulses of a test fluid stream directed through the instrument.

This invention features an automatic calibration system for an apparatus that measures the presence of a selected component in a test fluid sample. The system includes a transparent test fluid holder having an inlet and an outlet for conducting a test fluid into and out of the holder. There is a transparent calibration element immersed in the test fluid in the holder and including a first sealed compartment that contains a full scale calibration standard and a second sealed compartment that contains a zero calibration standard. There are means for directing a pulsed flow of the test fluid through the holder from the inlet to the outlet to reciprocate the calibration element within the holder. A light source is directed at the holder for establishing an incident beam of light that sequentially strikes the full scale standard, the zero standard and a test fluid sample as the calibration element reciprocates through the holder. Means are directed at the holder for sensing the light emitted from the full scale and zero calibration standards and the test fluid sample and for generating respective signals representative of the intensity of the emitted light. There are means for processing the respective signals to determine a calibrated measure of the selected component in the fluid sample.

In a preferred embodiment the holder includes a cuvette. The inlet is formed proximate a lower end of the cuvette and the outlet is formed proximate an upper end thereof. The calibration element may include a third open compartment that contains the test fluid sample.

The calibration element preferably reciprocates generally vertically between the upper and lower portions of the holder. The first and second compartments are juxtaposed with one of the compartments located vertically above the other compartments. The third compartment may have a generally cup-shaped configuration with an open upper end. Port means may be formed in the third compartment below the open upper end.

The tolerance between the calibration element and the holder is preferably such that the pulsed flow of fluid through the holder creates a laminar fluid flow between the calibration element and the holder. The calibration element and the holder may have complementary cylindrical shapes. The means for directing may include a pulsating pump.

The means for processing may include means for subtracting a signal representative of the intensity of the light emitted by the zero calibration standard from a signal representative of the intensity of the light emitted by the test fluid sample to provide a first zero-compensated measurement. Means may also be provided for subtracting the signal representative of the intensity of the light emitted by the zero calibration standard from a signal representative of the intensity emitted by the full scale calibration standard to provide a second zero-compensated measurement. The first zero-compensated measurement is divided by the second zero-compensated measurement to provide a compensated ratio and the compensated ratio is multiplied by the full scale compensation standard's predetermined value to provide the calibrated measurement. The means for processing may further include means for compensating for the internal offset on the respective signals. The means for sensing may detect emitted light and generate representative signals during vertical descent of the calibration element. Means may be provided for synchronizing the means for directing and the means for sensing and generating such that the emitted light is sensed at predetermined time intervals during each pulse cycle of the means for directing.

Preferably, the automatic calibration system is incorporated in a turbidimeter or similar appliance.

BRIEF DESCRIPTION OF THE DRAWINGS

Other objects, features and advantages will occur from the following description of a preferred embodiment and the accompanying drawings in which.

DETAILED DESCRIPTION OF PREFERRED EMBODIMENTS

The automatic calibration system of this invention may be employed in a variety of devices that measure the presence of a selected component in a test fluid sample. One preferred application, described below, is in a turbidimeter for performing nephelometric measurements of filtered water. Such instruments are widely used in water treatment facilities. The calibration system may also be employed with effective results in photometers and instruments for measuring the presence of a particular gas in a test fluid. Although liquids are tested in the embodiments described below, the test fluid may also comprise various vapors and gases.

In test liquid applications, the system comprises a transparent test liquid holder such as a cylindrical cuvette. The cuvette is preferably constructed of a transparent glass or plastic of the type that is commonly used in turbidimeters and similar devices. An inlet is formed proximate the bottom of the cuvette and an outlet extends from the top thereof. The precise manner in which the inlet and outlet are formed is not a limitation of this invention. Normally, they will be attached to the cuvette through suitable fittings that, for example, may resemble the cap disclosed in pending U.S. application Ser. No. 008,574. Alternatively, the inlet and outlet may be connected directly and unitarily to the cuvette. Various other forms of attachment will be apparent to those skilled in the art. The cuvette may be arranged in orientations other than vertical, although vertical is preferred because it takes advantage of the pulsed flow that is described below.

A transparent, preferably cylindrical calibration element is immersed in a test liquid in the holder. The calibration element is composed of a suitable glass or plastic material and is designed to reciprocate in a generally vertical direction within the cuvette. Reciprocating movement of the calibration element within the cuvette or other holder is accomplished by introducing a pulsed flow of test liquid though the holder from the inlet to the outlet. In nephelometric applications the liquid being tested is often water, although the invention is equally effective for use with other liquids. This pulsed flow is achieved by using a pulsating pump that is attached to a source of the test liquid. This pump can be a bellows, peristaltic, diaphragm or other commercially available variety of pump. The pump exhibits an exhaust stroke that pushes test liquid through the holder, thereby causing the calibration element to rise within the holder. Subsequently, the pump exhibits an intake stroke, which drains water from the holder and causes the calibration element to drop within the holder. A laminar flow is created between the reciprocating calibration element and the holder, which hydraulically cleans these components.

The system also includes an incandescent light source and a complementary sensor that are directed at the holder in a conventional manner. In a turbidimeter, these components are arranged at a 90° angle about the cuvette. However, in a photometer or other device that measures light transmission/absorption, the light source and sensor are normally arranged at a 180° angle relative to the holder. The light source and the sensor are conventional elements that are commercially available and known to those skilled in the art. In alternative embodiments, the light source may include non-incandescent means such as LED's and other non-incandescent lamps.

The transparent calibration element includes at least two sealed components, which contain a full scale calibration standard and a zero calibration standard, respectively. These calibration standards are, again, conventional, commercially available items. The full scale standard is selected according to the size of the component which is to be measured. In nephelometric applications, common full scale standards have values of 10 N.T.U. and 100 N.T.U., although other values may be employed within the scope of this invention. A preferred full scale standard for nephelometric applications comprises divinyl benzene particles suspended in pure water. A preferred zero reference standard comprises pure deionized water that is filtered of particles larger than 0.2 microns.

Preferably, the calibration element also includes a third compartment having an open end for accommodating a sample of test liquid. This third compartment is formed unitarily with the sealed compartments and preferably includes an open upper end and a pair of ports formed in the sides of the element.

During each pulse cycle, the calibration element is reciprocated by the pulsed liquid stream past the light source. An incident beam from the light source sequentially strikes the full scale and zero standards in the sealed compartments and the test sample in the cup-shaped compartment. At predetermined intervals, typically set by a microprocessor, the sensor detects the light emitted from the three compartments. For purposes of this specification, in nephelometric applications, the emitted light means the light scattered at 90° by the incident liquid. In a photometer or other instrument where the light source and sensor are arranged at 180°, emission refers to the light transmitted through the incident liquid. It should be understood that emission refers to any of the various ways, including scattering, transmission, etc. in which light may be projected from the calibration standards and test samples to the instrument's sensor.

A microprocessor or other signal processing means is programmed to automatically calibrate the instrument for each pulse cycle. Such means may comprise an analyzer as described in pending application Ser. No. 008,574. Initially, the instrument is normalized to compensate for internal offset of the electrical components (i.e. the A/D converter). Then, for each pulse, the intensity of the light emitted at predetermined times from the full scale and zero calibration standards and the test sample is sensed. Signals are generated to represent the intensity of the sensed light from each of the incident liquids. These intensity signals are then processed to provide a calibrated measure of the presence of the selected component in the test sample. Specifically, this measurement is derived according to the following formula:

$$\frac{T'-Z'}{FS'-Z'} \times \text{Predetermined Full Scale Standard Value}$$

where $T'$=Normalized Intensity of the Test Sample;
$Z'$=Normalized Intensity of the Zero Calibration Standard;
$FS'$=Normalized Intensity of Full Scale Standard; and
$FS$=Predetermined Full Scale Standard Value Through the use of the above formula, the system automatically calibrates the turbidimeter or other device during each pulse cycle. For a turbidimeter, the cycle is typically one cycle per second, although other cycles are acceptable. As a result, measurements of the selected component are continuously and automatically updated. The need for manual calibration and human intervention are reduced considerably.

Figure 1:
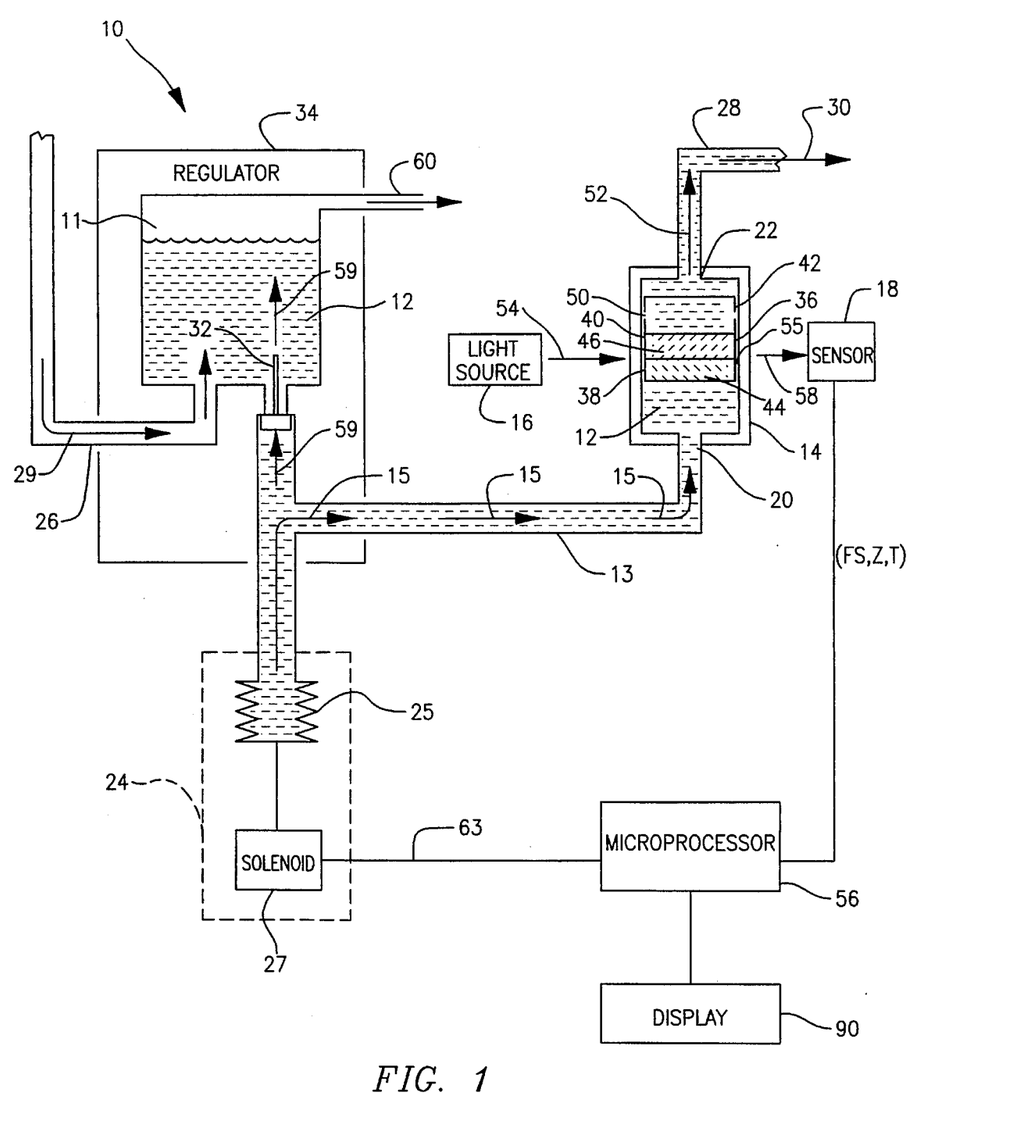
FIG. 1 is a schematic view of the calibration system of this invention during the pump exhaust stroke, with the calibration element in an elevated position within the test liquid holder.
Figures 2, 3:
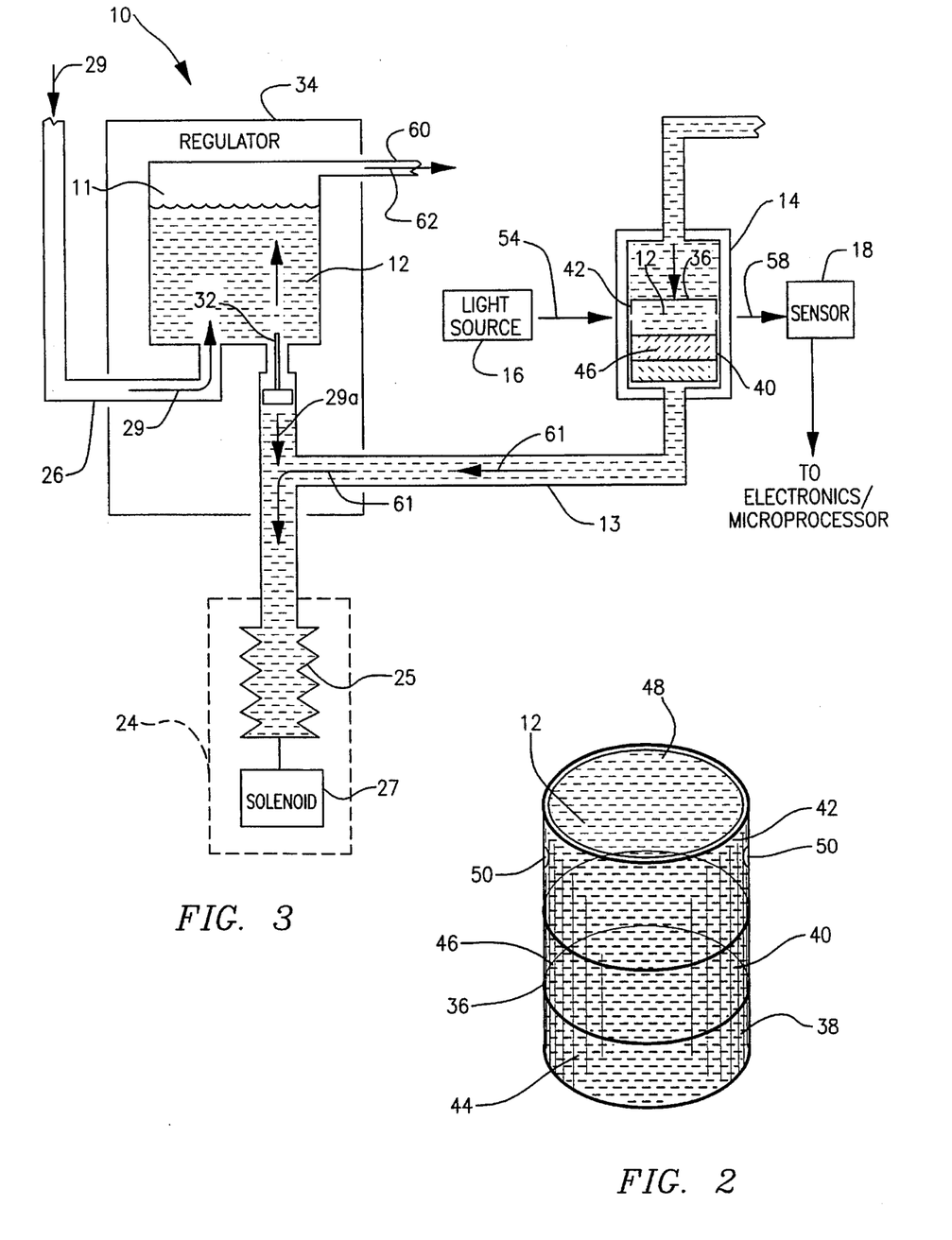
FIG. 2 is a perspective view of a preferred calibration element according to this invention.
FIG. 3 is a schematic diagram of the calibration system during the pump intake stroke, with the calibration element in a lowered position within the test holder.
Figure 4:
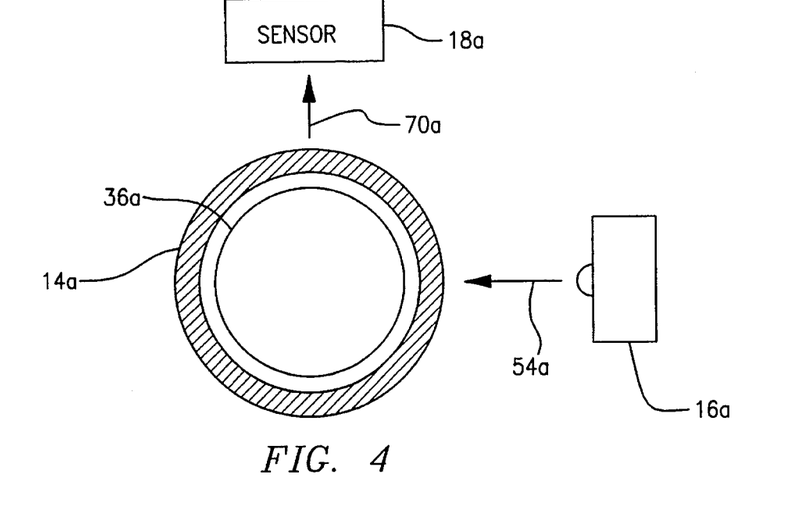
FIG. 4 is a diagramatic top view of the calibration system employed in a turbidimeter, with the light source and sensor arranged at a 90° angle to one another.

There is shown in FIG. 1 a calibration system 10, which is incorporated in an apparatus for measuring the presence of a selected component in a test liquid sample 12 within a transparent test liquid holder 14. The apparatus may comprise a turbidimeter, photometer or similar instrument wherein an incident light beam is used to measure component levels. In FIGS. 1 and 3, a standard light source 16 and sensor 18 are arranged at an angle of 180° relative to holder 14. Such orientations are normally employed in photometers and other devices for measuring light transmission and/or absorption. Alternatively, as depicted in FIG. 4, the light source 16a and sensor 18a may be arranged at a 90° orientation relative to the test liquid holder 14a. In such applications, the instrument is normally used to detect turbidity of the liquid sample within holder 14a.

Holder 14, FIG. 1, comprises a cylindrical cuvette. An inlet 20 is formed into the bottom of cuvette 14 and an outlet 22 is attached to the top of the cuvette. Test liquid 12 is introduced into cuvette 14 through inlet 20 by a pulsating pump 24. The pump includes a bellows 25 that is operated by a solenoid 27. More particularly, pump 24 directs a pulsed flow of test liquid 12 in the direction of arrow 29 through a line 26 and into a compartment 11 of a Weir regulator 34. From there, liquid 12 is pumped through a check valve 32 and into conduit 13. The liquid proceeds through conduit 13, in the direction of arrow 15, and through inlet 20 into cuvette 14. Test liquid 12 flows through cuvette 14 and is discharged therefrom through outlet 22. From there, the test liquid is drained through line 28 in the direction of arrow 30. Check valve 32 and a regulator 34 operate when required, in the manner described more fully below, to restrict and/or redirect the pulsed flow of liquid through the instrument.

A cylindrical calibration element 36 is immersed in liquid 12 within cuvette 14. A very thin gap 55 of approximately 0.005" is formed between the outer wall of element 36 and the inner wall of cuvette 14. Element 36, which is shown alone in FIG. 2, comprises a transparent cylindrical member that is neutrally buoyant within liquid 12. Element 36 includes a sealed bottom compartment 38, a sealed middle compartment 40 and an open upper compartment 42. These compartments are preferably unitarily connected and each has a cylindrical shape. Compartment 38 contains a liquid full scale calibration standard 44. Middle compartment 40 accommodates a zero calibration standard 46. Upper compartment 42 features a cup-like shape and includes an open top end 48. A pair of ports 50 are formed in the side of the upper compartment, approximately 180° apart. As a result, when test liquid 12 fills cuvette 14, as shown in FIG. 1, that liquid fills the interior of compartment 42.

Pump 24 features a pulsating operation that directs a cyclical, pulsed flow of test liquid 12 through cuvette 14. During each intake stroke of pump 24 (described more fully below in connection with FIG. 3), test liquid upstream of the pump is drawn in the direction of arrow 29 through a Weir regulator 34 and into pump bellows 25. Subsequently, on the exhaust stroke, shown in FIG. 1, bellows 25 compresses and pumps test liquid, in the direction of arrows 15, through conduit 13 and into cuvette 14 such that liquid fills the cuvette. Test liquid 12 is forced into gap 55 and enters ports 50 to fill compartment 42. Check valve 32 closes as indicated by arrows 59. This prevents test liquid 12 from being pumped back into regulator 34 from conduit 13. As a result, the contents of the pump bellows 25 are exhausted virtually entirely into cuvette 14. Excess test liquid is forced out of the cuvette through outlet 22 and drained in the direction of arrow 30. As test liquid is pumped through cuvette 14 in this manner, calibration element 36 is driven upwardly in the direction of arrow 52.

Light source 16 directs a continuous incident light beam 54 at cuvette 14. As calibration element 36 is driven upwardly within the cuvette, it passes through incident beam 54 until that beam strikes the full scale standard 44 within compartment 38. At a first predetermined time, a microprocessor 56 sends a signal to sensor 18, which directs the sensor to measure the intensity of a light beam 58 transmitted from standard 44. The sensor generates an intensity signal FS that is representative of the intensity of emitted light 58. This signal is provided to microprocessor 56 for the computations that are described below.

Pump 24 then performs an intake stroke, as shown in FIG. 3. Test liquid 12 is sucked into the pump from both regulator 34 and holder 14. In particular, check valve 32 opens and fresh test liquid enters pump 24 in the direction of arrow 29a. This liquid is held in the pump until the next exhaust stroke. At the same time, some of the test liquid 12 in cuvette 14 is drawn back into pump 24 in the direction of arrows 61. This causes the test liquid level and calibration element 36 to drop within cuvette 14. If, at any time, the head pressure of liquid entering in the direction of arrows 29 causes liquid 12 in regulator 34 to exceed the level of drain 60, the excess liquid is discharged through drain 60 in the direction of arrow 62. This controls the level of head pressure of liquid 12 such that the piston movement of element 36 is unaffected by head pressure and controlled by pump action alone.

As the level of test liquid 12 in cuvette 14 drops, the respective compartments of calibration element 36 pass downwardly through incident light beam 54. At a second predetermined time (again computed by the microprocessor) sensor 18 detects the light output or emission from zero standard 46 within compartment 40. A representative signal Z, FIG. 1, is transmitted to the microprocessor. Subsequently, as illustrated in FIG. 3, incident beam 54 strikes test liquid 12 within cup-shaped compartment 42 and output beam 58 from the test liquid strikes sensor 18. At a third predetermined time, the sensor measures the intensity of beam 58 and directs to the microprocessor 56 a third signal T, FIG. 1, which is representative of this intensity. After the three signals T, FS and Z have been derived, they are processed by microprocessor 56 in the manner described below, to determine the calibrated measurement for that particular pulse cycle.

Subsequently, pump 24 sequentially performs additional exhaust and intake strokes to continue the pulsed flow of test liquid 12 through cuvette 14. During each pulse, the calibration element 36 reciprocates upwardly and downwardly within cuvette 14. Pursuant to the exhaust stroke, fresh test liquid is introduced into compartment 42 through inlet ports 50. This fresh test liquid displaces the previously tested liquid, which is pumped out of cuvette 14 through outlet 22. As a result, a new signal T is subsequently derived each pulse cycle from the fresh test liquid in compartment 42. Fresh intensity signals FS and Z are likewise derived from the calibration standards during each cycle. The measurements of full scale, zero standard and test intensities are preferably taken during the downward, intake stroke of the calibration element. This is not a limitation of the invention, however, and the microprocessor may be programmed to take these measurements during the upstroke and at other points in the cycle. It should also be noted that for the purposes of this invention, it is not necessary that the full scale and calibration standards and the test sample be arranged for testing in the manner precisely described above. In alternative embodiments, the position of the full scale and zero standards may be reversed. Indeed, the position of the test sample relative to the two standards may be changed. However, the sequence described above discloses a very convenient positioning for the test sample and permits a new fresh test sample to be effectively measured during each pulse.

As previously described, during each pulse, test liquid 12 is forced into the annular gap 55 between calibration element 36 and the interior wall of cuvette 14. The tolerance between the calibration element and the inner wall of the cuvette is sufficiently small (e.g. 0.005") that, as the calibration element reciprocates, a laminar liquid flow is created between the calibration element and the cuvette. The laminar flow scours both the calibration element and the cuvette. As a result, the reciprocating element 36 performs hydraulic cleaning, which is repeated on each cycle of the pump. The glass components are kept clean and an improved signal and accuracy are provided.

As previously described, the embodiment shown in FIGS. 1 and 3 illustrates the light source 16 and sensor 18 arranged at 180° about cuvette 14. This is the orientation that is used by photometers and similar devices for detecting light transmission/absorption. In FIG. 4, light source 16a and sensor 18a are arranged at 90° relative to cuvette 14a. Calibration element 36a, which is constructed analogously to the element described in connection with FIGS. 1–3, contains calibration standards and a liquid test sample as previously described. As an incident light beam 54a strikes each of these liquids, a scattered light beam 70a is directed toward sensor 18a. At predetermined time intervals, the microprocessor directs sensor 18a to measure the intensity of scattered beam 70a. These intensities are again translated into signals T, FS and Z that are representative of the outputs from the full scale standard, zero standard and test sample, respectively. These outputs are then processed, as described below, to provide a calibrated measurement of turbidity.

The microprocessor determines the times at which the respective intensities are measured based upon the length of the pump cycle. In preferred embodiments this is 1 cycle/sec. At the lowermost point of the cycle, the pump solenoid 27 may send a synchronization pulse over line 63, FIG. 1, to microprocessor 56. The microprocessor then waits a precise period of time equal to approximately half a cycle (until the calibration element is elevated, as in FIG. 1) to take the first intensity measurement. In alternative embodiments, the microprocessor controls the entire operation including activation of pump 24.

Figure 5A:
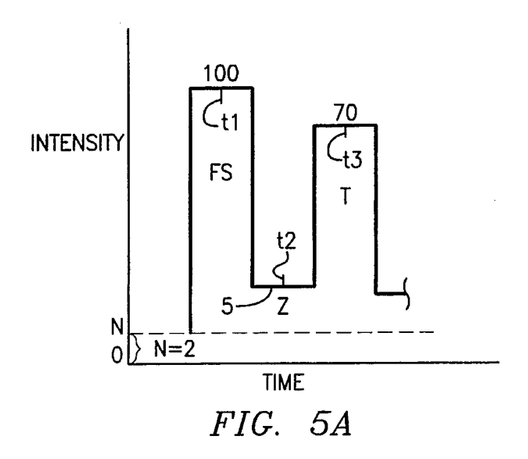
FIG. 5A is a graph of representative digital intensity signals generated during an initial pump cycle.
Figure 5B:
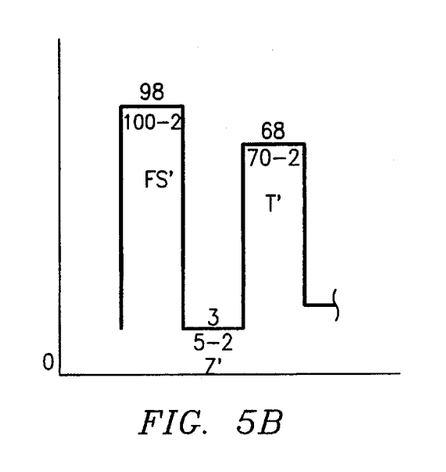
FIG. 5B is a graph of the signals of FIG. 5A after they have been normalized to compensate for electronic offset.
Figure 5C:
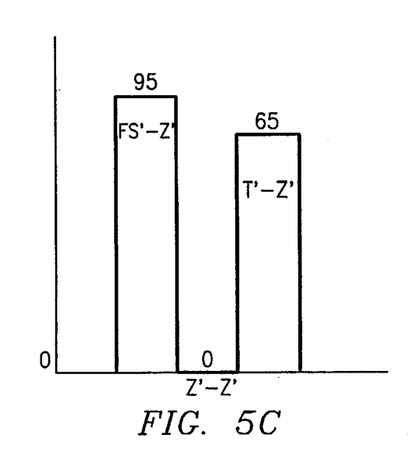
FIG. 5C is a graph of the signals of FIG. 5A after they have been zero compensated.
Figure 6A:
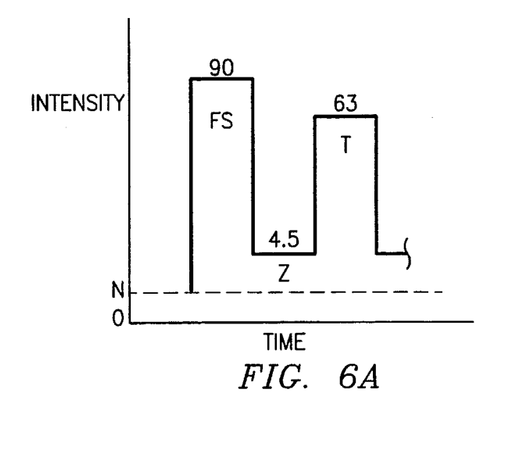
FIG. 6A is a graph of representative digital intensity signals generated during a subsequent pump cycle.
Figure 6B:
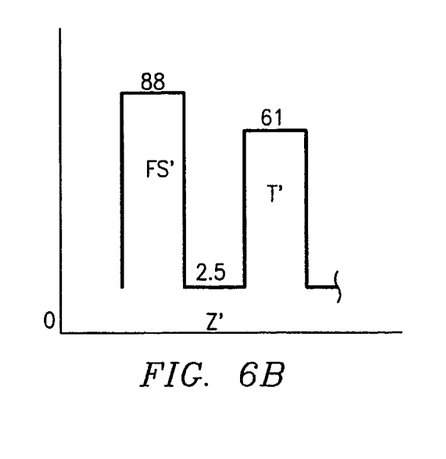
FIG. 6B is a graph of the signals of FIG. 6A after they have been normalized to compensate for electronic offset.
Figure 6C:
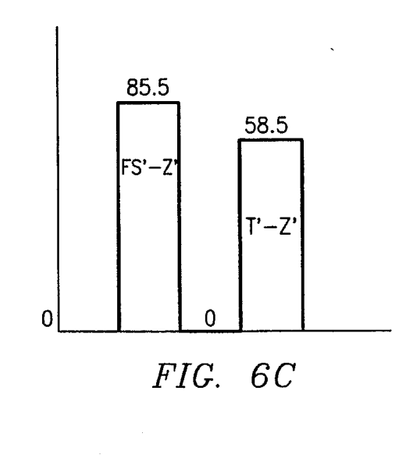
FIG. 6C is a graph of the signals of FIG. 6A after they have been zero compensated.

FIGS. 5A through 5C illustrate a representative digital output from turbidity sensor 18a during a pulse cycle at the beginning of the testing process. FIGS. 6A through 6C show a representative digital output at a later selected time. The values described are for illustration only and the principles of this invention apply equally for other values that may be measured by the system. The outputs that are depicted represent relative intensity levels. An intensity reading of true zero ("0") indicates that virtually no light is being scattered and that the liquid being tested has negligible turbidity. Increased outputs indicate increased levels of scattering and, therefore, increased turbidity. Initially, the turbidimeter must be normalized to compensate for electronic offset N, which typically results from the fact that the turbidimeter's A/D converter is offset from true zero. This offset is not affected by electronic deterioration or glassware contamination, but must be taken into consideration in order to perform consistently calibrated measurements. The system's software is designed to factor this offset into the computations. The offset value must be added algebraically to (i.e. subtracted from) the actual intensity measurements in order to perform the appropriate calculations required for making a calibrated measurement. In FIG. 5A, the offset value N equals 2. That value must be subtracted from each output to compensate for the offset. The initial raw output signal FS from the full scale standard is 100. Subsequently, the initial signal Z from the zero standard is 5 and the output signal T from the test liquid measures 70. It should be noted that although the zero standard is extremely pure water (which should theoretically have no turbidity), that standard almost never provides a reading of absolute zero. The water molecules and the glass of the sealed compartment holding the zero standard will almost always provide some measurable output signal. Accordingly, in this example, the output signal of the zero standard is 5.

FIGS. 5B and 5C illustrate the output signals as they are processed to calibrate this invention. Specifically, FIG. 5B depicts adjusted signals FS', Z' and T' wherein the electronic offset has been normalized for each signal by subtracting the offset value N=2 from each output value. FIG. 5C further depicts the signals after compensation has been made for the output (3) from the zero calibration standard. These calculations and their significance in calibrating the instrument are explained more fully below in connection with FIG. 7.

The graphs of FIGS. 6A through 6C illustrate the output signals FS, Z and T during a subsequent pulse cycle. The measured values for these signals, as seen in 6A are 90, 4.5 and 63, respectively. This 10 percent decrease represents light source deterioration or some other contamination or output falloff in the system. The offset-normalized and zero compensated signals generated during this cycle are shown in FIGS. 6B and 6C, respectively. These signals are derived in the manner described below. The output signal deterioration affects the measurements from the calibration standards and the sample equally. The system is calibrated as described below so that the deterioration or contamination does not disrupt the accuracy of the test sample measurement.

Figure 7:
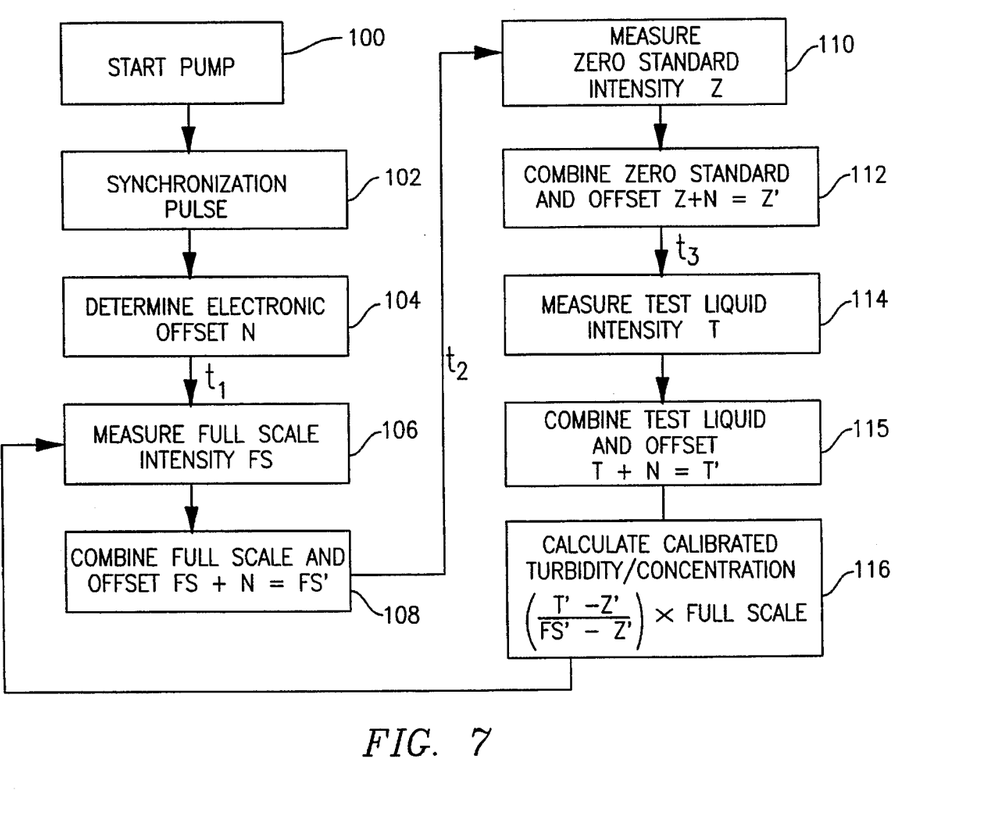
FIG. 7 is a block diagram illustrating a program for calculating a calibrated turbidity/concentration measurement using the system of this invention.

The microprocessor is programmed to perform the calibrated measurements in the manner shown in FIG. 7. In the following example, the output values of FIGS. 5A through 5C and 6A through 6C are used in the program. However, it should be understood that other outputs may be substituted equally effectively. Initially, pump 24 is started, step 100. The pump may be commenced by a signal from microprocessor 56, FIG. 1, over line 63. Alternatively, upon commencement of the pump's intake stroke, a synchronization pulse 102, FIG. 6, may be sent from the pump to the microprocessor. Initially, the microprocessor determines the electronic offset N, step 104 through a process built into the A/D converter. In a preferred embodiment, this is performed by a Maxum Max 132 integrated circuit or analogous circuitry. All subsequently sensed output signals are compensated for accordingly. This is accomplished using conventional software. At a predetermined time t1 after the synchronization pulse is received, the microprocessor directs sensor 18a to measure the full scale intensity and to generate a representative signal FS, step 106. This signal and the offset value N are combined to provide a normalized full scale signal FS' according to the following formula:

$FS'=FS+N$ (step 108)

At a second predetermined time t2, the microprocessor directs the sensor to measure the intensity of the signal from the zero calibration standard and to generate a representative signal Z, step 110. This signal is normalized by the microprocessor according to the formula:

$Z'=Z+N$ (step 112);

wherein Z' represents the normalized zero standard signal

At a third predetermined time, t3, the test liquid intensity is measured and a representative sample T is generated, step 114. This signal is similarly compensated for by the microprocessor, to provide normalized signal T', according to the formula $T'=T+N$ (step 115)

The microprocessor then takes the resultant signals FS', Z' and T' and derives a first zero compensated signal T'-Z' and a second zero compensated signal FS'-Z'. These signals compensate for the intensity that is generated even by the zero standard. The first and second zero compensated signals are processed, in step 116, according to the following formula:

Calibrated measurement (e.g. Turbidity) =

$$\frac{(T'-Z')}{(FS'-Z')} \times \text{Full Scale Standard Value}$$

This constitutes the calibrated turbidity measurement of the sample. The program returns to step 106 and the above computations are repeated for each pulse cycle of the sample stream. Subsequent deviations in the calibrated turbidity reading should strictly represent variations in the amount of the selected constituent present in the sample and should not comprise variations due to deterioration of the electronics or fogging or other contamination of the test liquid holder. The calibrated turbidity reading is updated for each cycle on an appropriate display 90, FIG. 1. Representative displays are shown in Ser. No. 008,574.

Application of the above formulas in a turbidimeter may be illustrated using the representative values shown in FIGS. 5A through 5C and 6A through 6C. For this example, it may be assumed that the full scale standard has a predetermined value of 10 N.T.U. The output intensity FS, FIG. 5A, is measured in step 106 as 100. This value is then normalized by subtracting the electronic offset:

$FS'=FS+N=100+(-2)=98$

The output signals, FIG. 5B, representing the zero calibration standard and test sample are similarly normalized as follows:

$Z'=Z+N=5-2=3$ $T'=T+N=70-2=68$

Zero compensated signals are derived as shown in FIG. 5C and the calibrated turbidity (CT) is calculated as follows:

$$CT = \frac{T-Z}{FS'-Z'} \times \text{(Full Scale Value)} =$$

$$\frac{68-3}{98-3} \times 10 \, N.T.U. = \frac{65}{95} \times 10 \, N.T.U. = 6.84 \, N.T.U.$$

During subsequent cycles, entirely different output signals may be derived to represent the full scale standard output, the zero standard output and the test sample output. If the turbidity of the test sample remains constant, the output signals should deviate equally. The changed values should result strictly from contamination or deterioration of the optics/electronics. For example, in FIGS. 6A through 6C, the output values for zero standard, full scale standard and test sample drop by 10% apiece. The full scale value FS is 90%, zero standard value Z is 4.5 and the test sample value T is 63. According to the program of FIG. 7, each of these values is normalized by compensating for the internal offset. Again, a value of 2 is subtracted from each of the output signals. Accordingly, offset normalized signals FS', Z' and T', FIG. 6B, are calculated as follows:

$$FS'=FS-N=90-2=88$$

$$Z'=Z-N=4.5-2=2.5$$

$$T'=T-N=63-2=61$$

The signals are zero compensated as shown in FIG. 6C:

$$T'-Z'=61-2.5=58.5$$

$$FS'-Z'=88-2.5=85.5$$

The calibrated turbidity CT is then calculated as follows:

$$CT = \frac{T-Z}{FS'-Z'} \times$$

$$\text{(Full Scale Value)} = \frac{58.5}{85.5} \times \times 10 \, N.T.U = 6.84 \, N.T.U.$$

Accordingly, the calibrated turbidity remains constant despite the change in output signals. This indicates that the system is properly calibrated. If there is a subsequent increase or decrease in turbidity of the test liquid, this should be reflected in a corresponding change in the output value for T only. The remaining values FS and Z will be unaffected. For example, if, during a subsequent pulse, the test liquid sample exhibits an output T of 72 instead of 70, but the calibration standard outputs Z and FS remain the same, this indicates an increased amount of scattering and increased turbidity in the sample. The calibrated turbidity would be calculated as follows:

$$CT = \frac{T-Z}{FS'-Z'} \times \text{Full Scale Value} =$$

$$\frac{70-3}{98-3} \times (10 \, N.T.U) = \frac{67}{95} \times (10 \, N.T.U.) = 7.05 \, N.T.U.$$

This variation would indicate an increased turbidity in the system of 0.21 N.T.U., which would be indicated on the instrument's display 90, illustrated in FIG. 1.

Because the test samples and calibration standards employ the same container, signal variations are not introduced into the system due to the use of different glassware for testing and calibration. This improves the calibration accuracy considerably. It also should be noted that because the calibration standards are measured at the same temperature, constituent particle size is affected equally by temperature variations. The process is thereby temperature compensated, in contrast to prior systems wherein temperature differences between the test sample and calibration standard may result in faulty readings.

Although specific features of the invention are shown in some drawings and not in others, this is for convenience only, as each of the features may be combined with any or all of the other features in accordance with the invention.

Other embodiments will occur to those skilled in the art and are within the following claims.

I claim:

1. An automatic calibration system for an apparatus that measures a presence of a selected component in a test fluid sample, said system comprising:

a transparent test fluid holder including an inlet and an outlet for conducting a test fluid into and out of said holder;

a transparent calibration element immersed in a test fluid in said holder and including a first sealed compartment that contains a zero calibration standard and a second sealed compartment that contains a full scale calibration standard;

means for directing a pulsed flow of said test fluid through said holder from said inlet to said outlet to reciprocate said calibration element within said holder;

a light source directed at said holder for establishing an incident beam of light that sequentially strikes said full scale standard, said zero standard and a test fluid sample as said calibration element reciprocates through said holder;

means directed at said holder for sensing light emitted from said full scale and zero calibration standards and said test liquid sample and generating respective signals representative of an intensity of said emitted light; and means for processing said respective signals to determine a calibrated measure of the selected component in said test fluid sample.

2. The system of claim 1 in which said holder includes a cuvette, said inlet being formed proximate a lower portion of said cuvette and said outlet being formed proximate an upper portion thereof.

3. The system of claim 2 in which said calibration element reciprocates generally vertically between said upper and lower portions of said holder.

4. The system of claim 3 in which said first and second compartments are juxtaposed with one of said compartments disposed vertically above another one of said compartment.

5. The system of claim 4 in which said calibration element includes a third compartment which is open and disposed above said first and second compartments for containing said test fluid sample therein.

6. The system of claim 5 in which said third compartment has a generally cup-like configuration with an open upper end.

7. The system of claim 6 in which port means are formed in said third compartment below said open upper end.

8. The system of claim 3 in which said means for sensing detects emitted light and generates intensity representative signals during vertical descent of said calibration element.

9. The system of claim 1 in which said calibration element includes a third compartment which is open and contains said test fluid sample.

10. The system of claim 1 in which a tolerance between said calibration element and said holder is such that the pulsed flow of fluid through said holder creates a laminar fluid flow between said calibration element and said holder.

11. The system of claim 1 in which said calibration element and said holder have complementary cylindrical shapes.

12. The system of claim 1 in which said means for directing include a pulsating pump.

13. The system of claim 1 in which said means for processing include means for subtracting a signal representative of an intensity of light emitted by the zero calibration standard from a signal representative of an intensity of the light emitted by the test fluid sample to provide a first zero compensated measurement, subtracting said signal representative of an intensity of light emitted by the zero calibration standard from said signal representative of intensity emitted by the full scale calibration standard to provide a second zero compensated measurement, dividing said first zero compensated measurement by said second zero compensated measurement to provide a compensated ratio and multiplying said compensated ratio by said full scale calibration standard's predetermined valve to provide said calibrated measure.

14. The system of claim 13 in which said means for processing further include means for compensating for an effect of internal offset on said respective signals.

15. The system of claim 1 further including means for synchronizing said means for directing and said means for sensing and generating such that said emitted light is sensed at predetermined time intervals during each pulse cycle of said means for directing.

16. An automatic calibration system for a turbidimeter comprising:

a transparent test liquid holder including an inlet and an outlet for conducting a test liquid into and out of said holder;

a transparent calibration element immersed in a test liquid in said holder and including a first sealed compartment that contains a zero calibration standard and a second sealed compartment that contains a full scale calibration standard;

means for directing a pulsed flow of said test liquid through said holder from said inlet to said outlet to reciprocate said calibration element within said holder;

a light source directed at said holder for establishing an incident beam of light that sequentially strikes said full scale standard, said zero standard and a test liquid sample as said calibration element reciprocates through said holder;

means directed at said holder at an angle of approximately 90° to an direction of said light source for sensing light scattered respectively from said full scale and zero calibration standards and said test liquid sample and generating respective signals representative of an intensity of the scattered light; and means for processing said respective signals to determine a calibrated turbidity of said liquid test sample.

* * * * *